United States Patent [19]

Chorev

[11] Patent Number: 5,242,680
[45] Date of Patent: Sep. 7, 1993

[54] THIOL-REACTIVE MALEIMIDO-BASED RADIOLABELING REAGENTS

[75] Inventor: Michael Chorev, Jerusalem, Israel

[73] Assignee: Merck & Co., Inc., Rahway, N.J.

[21] Appl. No.: 749,392

[22] Filed: Aug. 23, 1991

[51] Int. Cl.$^5$ ............... A61K 49/02; C07D 207/448
[52] U.S. Cl. .................................. 424/1.1; 548/548
[58] Field of Search ............ 424/1.1; 548/548, 549; 530/391.5, 402

[56] References Cited

U.S. PATENT DOCUMENTS

| | | | |
|---|---|---|---|
| 3,265,708 | 8/1966 | Stiteler | 548/549 |
| 3,337,584 | 8/1967 | Knock | 548/548 |
| 4,542,225 | 9/1985 | Blatter et al. | 548/548 X |
| 4,735,792 | 4/1988 | Srivastava | 424/1.1 |
| 4,885,153 | 12/1989 | Wilbur et al. | 424/1.1 |
| 4,994,557 | 2/1991 | Kassis et al. | 548/549 X |
| 5,045,303 | 9/1991 | Wilbur et al. | 424/1.1 |

FOREIGN PATENT DOCUMENTS

| | | | |
|---|---|---|---|
| 149253 | 11/1980 | Japan | 548/549 |

*Primary Examiner*—Robert L. Stoll
*Assistant Examiner*—John M. Covert
*Attorney, Agent, or Firm*—Mark R. Daniel; Joseph F. DiPrima

[57] ABSTRACT

Novel thiol-reactive maleimido-based radiolabeling reagents are disclosed which are useful for binding and receptor studies and assays. The reagents are also useful as diagnostic imaging agents, and as radiotherapeutic drugs.

15 Claims, No Drawings

THIOL-REACTIVE MALEIMIDO-BASED RADIOLABELING REAGENTS

BACKGROUND OF THE INVENTION

Molecular tagging of biomolecules provides an indispensable tool used in many fields such as biochemistry, molecular biology, immunology and medicine. Radioiodinated bio-ligands and bio-macromolecules are the most abundant examples of molecular tagging. Because of its high specific activity, significant half life and relatively simple preparative procedures radioiodinations are among the most frequent labeling approaches employed.

The high specific activity and the significant half life of $^{125}I$ makes this isotope especially suitable for labeling and tracing of minute amounts of biomolecules. Some of the major research areas which rely heavily on radioiodinated preparations include receptor studies, affinity labeling and immunochemistry. The methods available today for radioiodination include direct methods where in situ oxidation of $^{125}I$ by a variety of oxidants is carried out in the presence of the compound being subjected to radioiodination, and indirect methods where pre-radioiodinated reagents are used to N-modify amino functions in compounds of interest.

Some of the methods of direct radioiodinations include chloramine T (N-chloro-4-methylbenzensulfonamide sodium salt) (See Greenwood, F. C. et al., *Biochem. J.* 89, (1963)), Iodo-Beads (polymeric chloramine T) (See Markwell, M.A.K., *Anal Biochem.* 125, (1983), Iodo-Gen (1,3,4,6-tetrachloro-3a-6a-diphenylglycoluril) (See Fraker, P. J. et al., *Biochem. Biophys. Res. Commun.* 80, (1987)), Lactoperoxidase (See Thorell, J. I. et al., *Biochim. Biophys. Acta* 25, (1971)), and electochemical oxidation (Teare, F. W. et al., *Intl. J. Appl. Rad. Isot.* 29, (1978)). These radioiodinations occur on aromatic moieties such as phenolic, imidazolyl and indolyl which are sufficiently active toward electrophilic substitution. In general, these oxidative methods lead to complex reaction mixtures containing radioactive components (See Koshland, M. E. et al. J. Biol. Chem. 238, (1963)).

Polyiodinations, oxidations, reductions (when reducing agents such as sodium metabisulfite are used to decompose excess of the oxidizing reagent) and the presence of multiple reactive moieties in a single biomolecule accompanied by the lack of sufficient selectivity of the radioiodinating reagent, result in heterogeneous preparations which require tedious purifications.

The indirect radioiodination employs pre-labeled reagents thus avoiding the damage caused by the direct iodinations (See Bolton, A. E. et al., *Biochem.* J. 133, (1973) and Wood, F. T. et al., Anal. *Biochem.* 69, (1975)). To date only the mild acylating reagent N-succinimidyl 3-(4-hydroxy, 5-[$^{125}I$]iodophenyl) propionate (known as the Bolton-Hunter reagent) is used for achieving non-oxidative indirect radioiodinations (See Bolton, A. E. et al., *Biochem.* J. 133, (1973)). The Bolton-Hunter reagent acylates predominantly primary ε-amino functions of lysine residues and to a lesser extend N-terminal α-amino functions. In spite of the mild conditions under which the N-acylation by Bolton-Hunter reagent occurs, the heterogeneity of radioiodinated product results from the high abundance of multiple lysine residues in peptides and proteins which leads to hetero-mono and hetero-poly radioiodinated tracer (See Bolander, Jr. F. F. et al., Biochem. 14, (1975)).

Furthermore, the susceptibility of the N-succinimidyl ester in the Bolton-Hunter reagent to hydrolysis limits it shelflife and calls for introduction of large molar excess of substrate to achieve efficient incorporations. This has obvious disadvantages when the substrate for labeling is a material which is hard to obtain. Under forcing conditions, where excess of Bolton-Hunter reagent is employed, acylation of histidine and tyrosine residues may also occur (See Knight, L. C., Biochim. Biophys. Acta 534, (1978)).

It was, therefore, an object of this invention to develop an indirect, mild and highly selective radiolabeling method which combines the advantage of the high specificity of the maleimido moiety towards a sulfhydryl group which results in an efficient and quantitative addition of thiols across the activated double bond of the maleimido moiety to form a stable thio-ether. The specificity of this reaction coupled with both the low abundance of cysteine residues in many proteins and bioactive peptides, and the ease of introduction of a cysteine residue or thiol containing moiety into synthetic peptide analogs allows for selective and specific iodination. Based on the low abundance of cysteine in peptides and the specificity and high reactivity of a sulfhydryl function toward a maleimido moiety, it was an object of this invention to develop a novel approach to indirect radiolabeling of peptides containing sulfhydryl groups by using the maleimido-based reagents of this invention.

SUMMARY OF THE INVENTION

The present invention is directed to novel thiol-reactive maleimido-based radiolabeling reagents which are useful for binding and receptor studies. The present invention is further directed to the development of novel indirect radioiodination of bioactive pepitides based on the sulfhydryl-maleimido chemistry of this invention.

DETAILED DESCRIPTION OF THE INVENTION

The thiol-reactive maleimido-based compounds of this invention are those of Formula I:

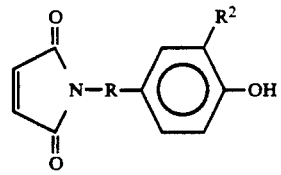

wherein:
R is

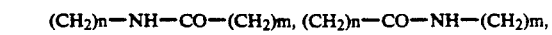

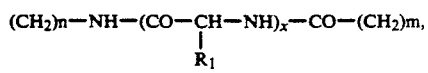

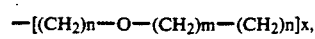

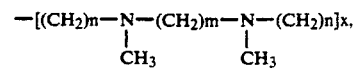

-continued

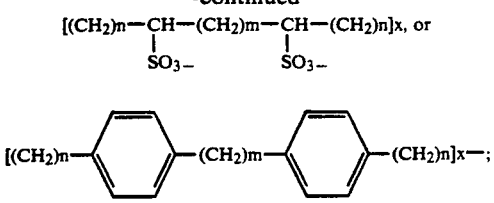

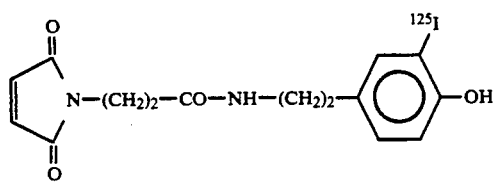

R[1] is neutral, charged +/−, hydrophobic or hydrophilic;
n is 0 to 2;
m is 0 to 2; and
x is 0 to 2.

The preferred compounds of this invention for use as radioiodolabeling reagents include:

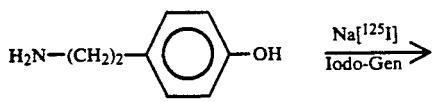 (A)

or

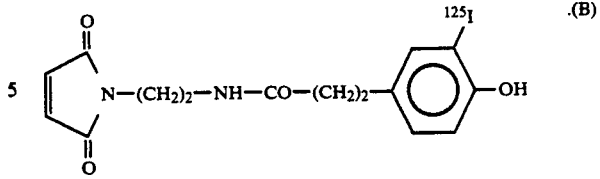 (B)

The thiol-reactive maleimido-based compounds of Formula I are useful in the indirect radiolabeling of cysteine containing peptides. Peptides which may be used for the indirect non-oxidative maleimido-based thiol-specific radioiodinating procedure are those which contain cysteine or could be modified to include either a cysteine residue or a sulfhydryl carrying moiety in its structure. Examples of such cysteine containing peptides include, but are not limited to, Tachykinins (substance P, Neurokinin A and Neurokinin B), Parathyroid Hormone (PTH), Parathyroid Hormone-related Protein (PTHrP), Bombesin, and Met-Enkephalin. The efficacy of radiodolabeling a cysteine containing peptide has been demonstrated on cysteine-containing analogs of Parathyroid hormone (PTH) and Parathyroid Hormone-related protein (PTHrP).

The radioiodolabeled compounds of this invention may be used for binding and receptor studies, in the development of assays, in autoradiography, as diagnostic imaging agents, and as radiotherapeutic drugs. Suitable radionuclides include $^{122}I$, $^{123}I$, $^{125}I$, $^{131}I$, $^{75}Br$, $^{77}Br$, $^{83}Br$ and $^{211}At$.

The compounds of Formula I may be prepared according to the reaction schemes as set forth below:

SCHEME II

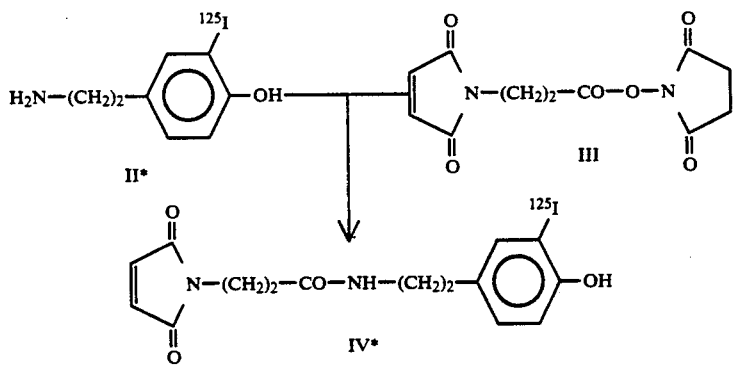

A.

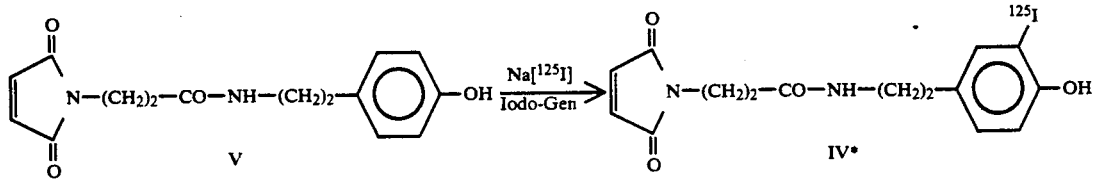

B.

-continued
SCHEME II
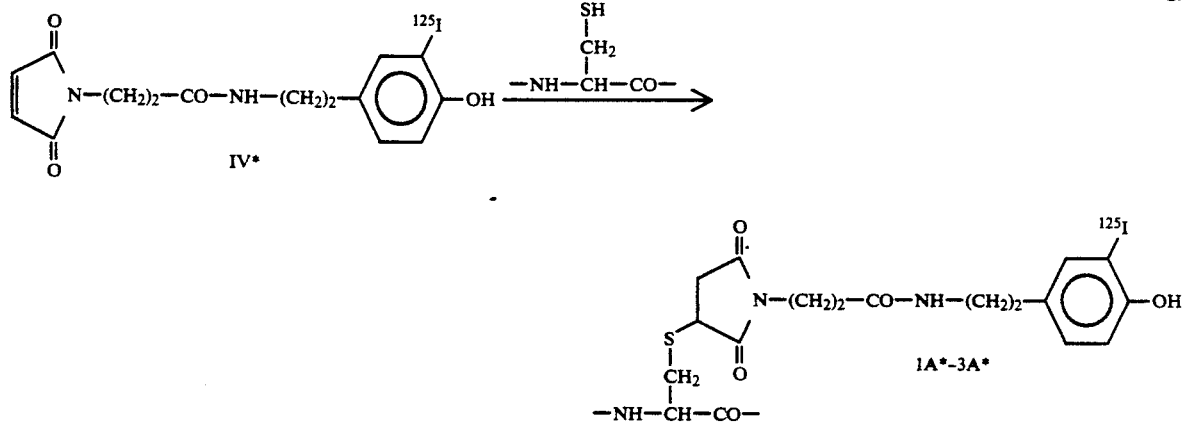
SCHEME III
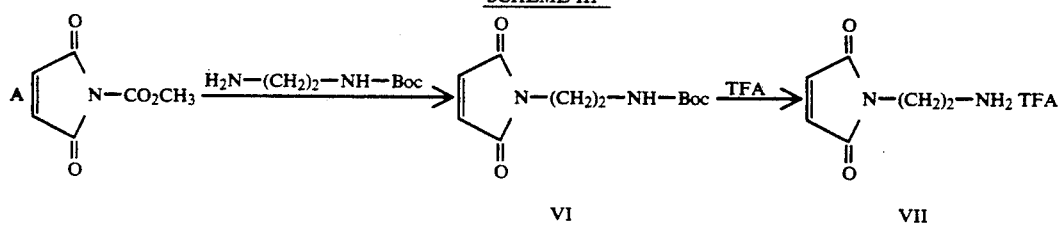
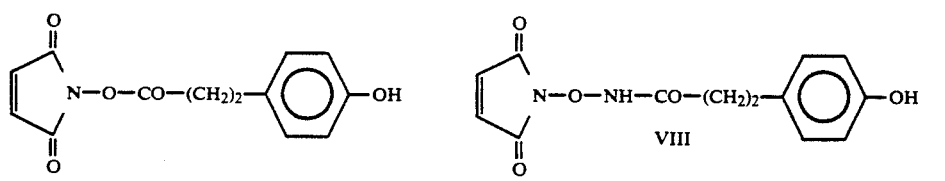
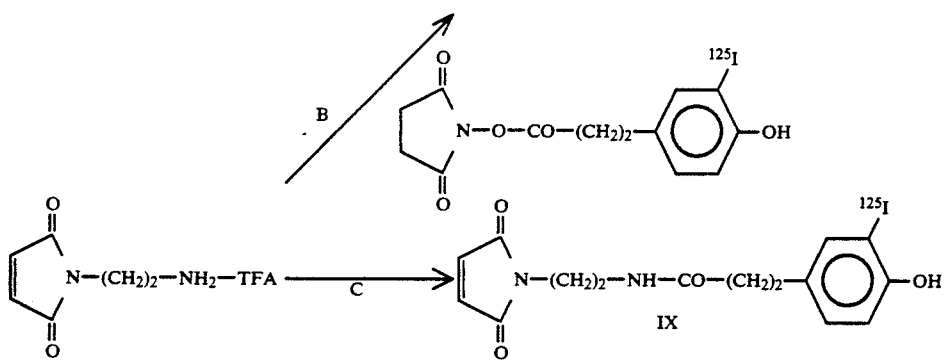
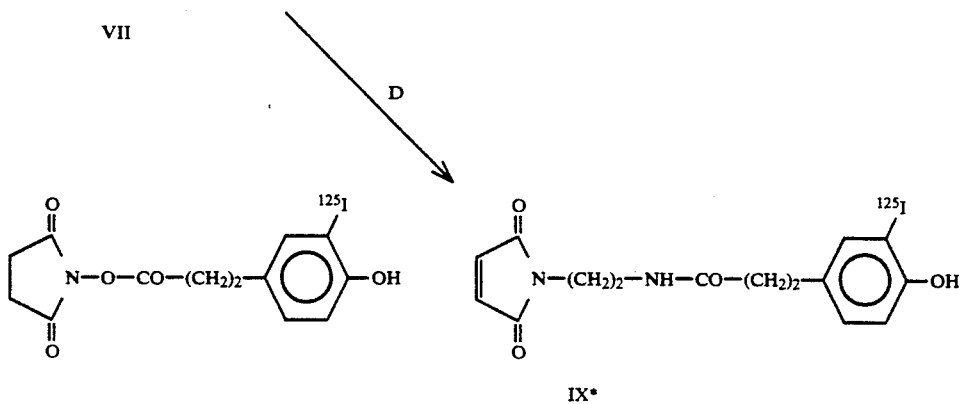

-continued
SCHEME III

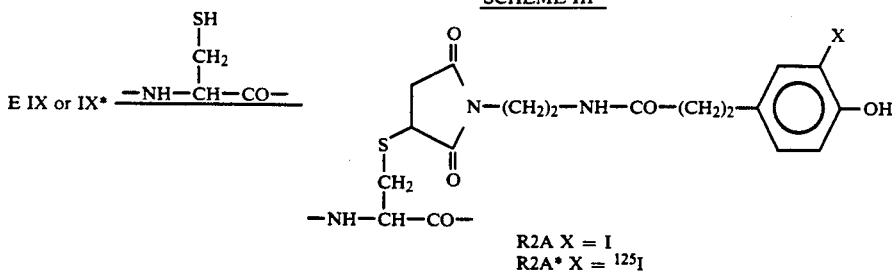

R2A X = I
R2A* X = $^{125}$I

SCHEME IV

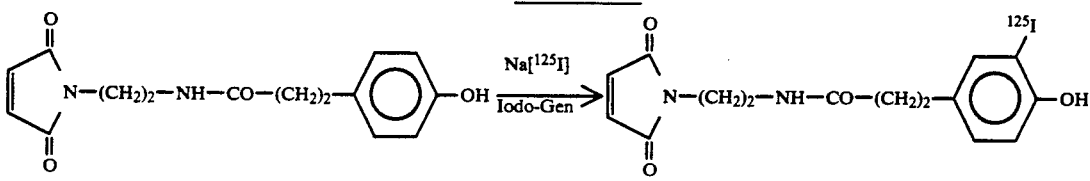

The reaction of N-succinimidyl 3-maleimidopropionate with 2-(4-hydroxyphenyl) ethylamine and N-succinimidlyl 3-(4-hydroxyphenyl)propionate with 2-maleimido-ethylamine yielded products that were subjected to Iodo-Gen-madiated radioiodinations yielding radioiodolabeling reagents A and B, respectively, which differ in the direction of the amide bond.

The incorporation of $^{125}$I$^-$ to produce A and B is carried out in high efficiency and results in mixtures which lend themselves to very fast and easy RP-HPLC purifications. The cold and radiolabeled malaimidio-containing reagents were used to modify cysteine-substituted analogs of PTH and PTHrP. For example, the following analogs were modified by the cold and radioactive maleimido-based reagents; PTH agonist [Nle$^{8,18}$,Lys$^{13}$($\epsilon$-Biotinyl),Tyr$^{34}$, Cys$^{35}$]bPTH(1-35)amide (3), PTHrP agonist ([Cys$^{35}$]PTHrP(1-35)amide (1) and PTHrP antagonist Ac[Cys$^8$,Leu$^{11}$,-D-Trp$^{12}$]PTHrP(8-34)amide (2). The cold Cys-modified analogs were used for physicochemical characterization and were tested in in vitro bioassays to establish their biological activity. In all cases an excellent maintenance of bioactivities was exhibited in either adenylate cyclase or receptor binding assays. The efficient, high yield radioiodinations of these analogs with A and B radioiodolabeling reagents were carried out overnight at 0° C., in neutral pH leading to simple reaction mixtures amenable to fast RP-HPLC purification. The identity of the radiolabeled analogs was estblished by co-elution with the corresponding cold iodolabeled analogs. The purified radiolabeled tracers were stable upon storage at −70° C. These tracers bind to a single binding site in human osteosarcoma B-10 cells in a non-cooperative, reversible and saturable manner with very high affinities (Kd=1-3 nM).

PTH and PTHrP analogs included in this study were designed on the basis of recent structureactivity relationship studies carried in our laboratories (see McKee, R. L., Endocrinol. 122, 30008-3010 (1988), Nutt, R. F., et al., Endocrinol. 127, 491-493 (1990), Horiuchi, N., et al., Science238, 1566-1568 (1987)). Cystein residues substituted positions in the peptide in a way which will not effect the PTH agonist-or antagonist-like activities. In the PTH and PTHrP agonist related analogs (1) and (3), respectively, we chose to extend the 1-34 sequence by a cysteine residue at position 35. Substitution of Leu$^8$ with Ac-Cys was the modification of choise in the PTHrP antagonist related analog 2.

Synthesis of 3'-maleimidopropionyl-3-iodotyramide (IV) was accomplished by the acylation of 3-iodotyramine (II) (see Fischer, A.G., et al., J. Biol. Chem. 240, 4338-4343 (1965)) with the commercially available N-succinimidyl 3-maleimido-propionate (III) following conditions described by Wunsch and coworkers (see Wunsch, E. et al., Biol. Chem. Hoppe-Seyler 366, 53-61 (1985)). The radiolabeling reagent 3'-maleimidopropion-3-[$^{125}$I]iodotyramide (IV*) was prepared by either a two step procedure (see method A in Scheme II) or a single step (see method B in Scheme II). Iodo-Gen mediated radioiodination of tyramine (I) is the first step in Method A. The same chemistry was employed to radiolabel directly the 3-maleimidopropiontyramide (V) as formulated in method B. In spite of the more lengthy and less convenient method A, both synthetic routes gave the radiolabeled alkylating reagent IV*.

In parallel, we developed an alternative approach which is summerized in Scheme III. Preparation of N-maleoyl ethylenediamine trifluoroacetate (VII) following TFA mediated acidolysis of the N-protected carbamate VI which was synthesized by a procedure similar to those described by Keller and Rudinger (see Keller, O. et al., Helv. Chim. Acta 58, 531-540 (1975)) (see route A in Scheme III). Reaction of this amine VII with a the succinimidyl esters derived from 4-hydroxyphenyl-, 4-hydroxy-3-iodo-phenyl-and 4-hydroxy-3-[$^{125}$I]-iodophenyl-propionic acid (Bolton-Hunter reagents) (see Bolton, A. E., et al., Biochem. J. 133, (1973), Rudinger, J. et al., Biochem. J. 133, 538-539 (1973), Michelot, R., et al., Biochem. Biophys. Res. Commun. 95, 491-498 (1980)) yielded reagents VIII, IX and IX*, respectively (see routes B-D in Scheme III). (insert Scheme III).

The purified peptide analogs 1-3 were used as substrates in the alkylation reaction by either the isolated 3-iodotyramide derivative IV or the RP-HPLC purified 3-[$^{125}$I]iodotyramide IV* to yield the adducts 1A-3A and 1A*-3A*, respectively. While the non-radioactive adducts 1A-3A were purified by preparative RP-HPLC, the radiolabled adducts 1A*-3A* were purified by analytical RP-HPLC. In a similar phasion the maleimido reagents obtained from the 4-hydroxyphenyl propionic acid, IX and IX*, were used to modify $Cys^8$-substituted PTHrP antagonist 2 to obtained either the non-radioactive or the radioiodinated adducts R2A abd R2A*, respectively. The only difference between 2A and 2A* and their corresponding isomers R2A and R2A*, respectively, amount to the reversal of the amide bond in the spacer connecting the 3-S-succinimidyl with the 4-hydroxy-3-iodophenyl moieties (R in R2A and R2A* denote the reversal of the amide bond direction).

The identity of the radiolabling reagents IV* and IX* and the radiolabled adducts 1A*-3A* and R2A* was established by co-elution of the peak of radioactivity and peak of UV absorbance at 214 nm following a co-injection of a the freshly prepared tracer with an aliquate of the non-radioactive adduct.

EXAMPLES

Examples provided are intended to assist in a further understanding of the invention. Particular materials employed, species and conditions are intended to be further illustrative of the invention and not limitative of the reasonable scope thereof.

Materials-Ultrapura-grade [$Nle^{8,18}$, $Tyr^{34}$]bPTH-(1-34)$NH_2$, N-Boc-L-Asp($\beta$-cHex)-OH, N-Boc-L-Lys($\epsilon$-N-Fmoc)-OH, N-Boc-$N^\pi$-Bom-L-His-OH were obtained from Bachem Inc. (Torrence, Calif.). The rest of the N-Boc-protected amino acid derivatives, p-methylbenzhydrylamine resin hydrochloride (1% cross-linked, 0.64 mmol nitrogen/g), N,N'-dicyclohexylcarbodiimide (DCC), 1-hydroxybenzo-tryazole, diisopropylethylamine (DIPEA), piperidine and trifluoroacetic acid (TFA) were purchased from Applied Biosystems Inc. (Foster City, Calif.). Dichloromethane (DCM) and N,N-dimethylformaide (DMF), both B&J brand, were purchased from Baxter Healthcare Co. (Muskegon, Mich.). Hydrogen fluoride was purchased from Matheson (Secaucus, N.J.). p-Cresol from Aldrich Chemical Inc. (Milwaukee, Wis.). Biotin, methoxycarbonylmaleimide and N-succinimidyl 3-maleimidopropionate were purchased from Fluka Chemie AG (Buchs, Switzerland). N-succinimidyl-3-(4-hydroxyphenyl)propionate was purchased from Pierce (Rockford, Ill.). Bovine serum albumin, Tris-HCl, phosphocreatine, creatine phosphokinase, GTP, isobutylmethylxantine, and Mg-ATP were obtained from Sigma (St. Louis, Mo.). Bovine kidneys were the gift of Baums Meat Packing Inc. (Hatfield, Pa.).

Biological Assays

SaSO-2/B10 cells cultures. The details of maintenance of this cell line in culture were reported previously (see Chorev, M., et al., Intl. J. Peptide & Protein Res. 36, 465-470 (1990)).

PTH Receptor Binding and Adenylate Cyclase Assays. Kidney-based assays were performed with bovind renal cortical membranes following the procedures previously described (see Goldman, M. E., et al., Endocrinol. 123, 1468-1475 (1988)). Bone-based assays were performed with human SaOS-2/B10 cell cultures. Cyclic AMP was measured using the reported procedure (see Rodan, S. B., et al., J. Clin. Invest. 72, 1511-1515 (1983)), including modifications reported previously (see Chorev. M., et al., Intl. J. Peptide & Protein Res. 36, 465-470 (1990)). Receptor binding affinities for PTHrP analogs were obtained using cells plated in 24-wall dished in RPMI 1640 medium supplemented with 1% BSA, 20 mM HEPES, pH 7.5, and 0.1% azide. [$Nle^{8,18}$, mono-$^{123}$I-$Tyr^4$]bPTH(1-34)$NH_2$ (50,000 cpm/well) was added to confluent monolayers in the absence or presence of varying amounts of analog in a final volume of 0.25 ml. Cultures were incubated at room temperature for 4 hours. Binding reactions were terminated by placing the cultures on ice and washing 4 times with ice cold phosphate buffered saline. Radioactivity associated with the cells was recovered by dissolving the cells in 1 ml of 1N NaOH.

Data analysis. Inhibition constants for binding ($K_b$) and adenylate cyclase ($K_i$) were calculated following a published method (see Cheng, Y. C., et al., Biochem. Pharmacol. 22, 3099-3108 (1973)).

Synthesis of Peptides and Labeling Reagents-The peptides; [$Cys^{35}$]PTHrP(1-35)$NH_2$ (1). Ac[$Cys^8$, $Leu^{11}$,D-$Trp^{12}$]PTHrP(8-34)$NH_2$ (2), and [$Nle^{8,18}$, $Lys^{13}$($\epsilon$-Biotinyl), $Tyr^{34}$, $Cys^{35}$-] bPTM(1-35)$NH_2$ (3) were synthesized on an Applied Biosystems 430A Automated Peptide Synthesizer using version 1.2 of the software, and a modification of Merrifield's solid phase procedure (see Merrifield, R. B. Adv. Enzymol, 32, 221-296 (1969)). The synthesis followed the reported procedure (see Chorev, M., et al., Intl. J. Peptide & Protein Res. 36, 465-470 (1990)) including the following modifications: After recoupling of each of the three arginines (residues 18-21) and histidines (residues 25 and 26) in the PTHrP-derived sequences (analogs 1 and 2), prior to the removal of the N$\alpha$-Boc protecting group, an acetylation of the residual free $\alpha$-amino groups was carried out employing DCC mediated acetic acid (114 ul, 2 mmol) coupling. Modification of $Lys^{13}$ by N $\epsilon$-biotinylation was carried out. The crude material obtained after HF cleavage was fractionated on a G-50 Sephadex column using a mobile phase of 50% acetic acid. The crude peptides were purified on a Waters $\delta$-Prep HPLC system using a Vydac protein C-18 column (15 u). The solvent system employed was A: 0.1% TFA in water-acetonitrile (19:1), B: 0.1% TFA in acetonitrile using a gradient of 15-40% (for analog 1) and 10-50% of B (for analogs 2 and 3) at a flow rate of 100 ml/min monitored at 214 nm. The yields of purified materials obtained from the synthesis were 153, 100 and 123 mg, for analogs 1-3 respectively.

EXAMPLE 1

3'-Maleimidopropion-3-iodo-tyramide (IV)

To an ice cold solution of 3-iodo-tyramine (preparation of II follows Ref. (see Fischer, A. G., et al. J. Biol. Chem. 240, 4338-4343 (1965)) (131.5 mg, 0.5 mmol) in DMF (1.5 ml) was added N-succinimidyl 3-maleimidopropionate (III) (133.1 mg. 0.5 mmol), diisopropylethylamine (87 ul, 0.5 mmol) and pyridine (39 ul, 0.5 mmol). After 1 hr at 0° C. the reaction mixture was stirred over night at room temperature. The residue obtained after removal of solvent under reduced pressure was taken in ethylacetate and extracted consecutively with a solution of 2% $KHSO_4$, brine, a solution of 5% $NaHCO_2$ and brine. The organic phase was dried over $Na_2SO_4$ and the solvent removed under reduced pressure. The residue was purified on $\delta$ Prep Vydac protein C-18 column; 214 nm; gradient 0-50% B in 120 min at a flow rate of 100 ml/min; 10 ml/fraction. The product came off the column at about 18–19% B. The pooled peak was dried under reduced pressure and the residue taken up in water and lyophilized to yield 48 mg (23.2%). RP-HPLC: t4.5 min and k'=13.20; Vydac protein C-18 (0.21×15 cm) 5u: 214 nm; A: 0.1% TFA in water-acetonitrile (19:1), B: 0.1% TFA in acetonitrile using gradient of 0–10% B in 30 min and flow rate of 1.5 ml/min.

EXAMPLE 2

3-maleimidopropiontyramide (V)

To an ice cold mixture of tyramine (274.4 mg, 2 mmol) and 3-maleimidopropionic acid (676.6 mg, 4 mmol) in DMF (2 ml) was added 1-ethyl-3-(3-dimethylaminopropyl)carbodiimide HCl (EDC) (383.4 mg, 2 mmol). The reaction mixture was stirred at room temperature over night. The residue obtained after removal of DMF under reduced pressure was taken up in ethylacetate and consecutively extracted with 1N HCl, brine, 5% solution of NaHCO and brine. The organic phase was dried over $Na_2SO_4$ and the solvent removed under reduced pressure to yield 220 mg of crude product. The crude product was purified on δ-Prep Vydac protein C-18 column; 214 nm; gradient 10–50% B in 200 min at a flow rate of 100 ml/min; 10 ml/fraction. The product eluted from the column at about 18–19% B. The pooled peak was dried under reduced pressure and the residue taken up in water and lyophilized to yield 130 mg (22.5%). RP-HPLC: $t_r$=13.7 and k'=9.53; Vydac protein C-18 (0.21×15 cm) 5μ; 214 nm; A: 0.1% TFA in water-acetonitrile (19:1), B: 0.1% TFA in acetonitrile using gradient of 0–50% B in 30 min and a flow rate of 1.5 ml/min. FAB-MS: Mw calcd. for $C_{15}H_{16}N_2O_4$ 287.29, found 289. Elemental analysis: % calcd./% Found: C 62.70/56.22; H 5.61/4.95; N 9.75/8.51.

EXAMPLE 3

Synthesis of N-tert butyloxycarbonyl-N'-maleoyl ethylenediamine (VI):

N-Boc-ethylenediamine (5.8 g, 36.25 mmol) was dissolved in a saturated solution of $NaHCO_3$ (150 ml) and cooled to 0° C. N-Methoxycarbonylmaleimide (5.62 g, 36.2 mmol) was added to the stirred solution. After 10 min the reaction mixture was diluted with water (300 ml) and stirred for 30 min, after which a second portion of N-methoxycarbonylmalemide (1.4 g, 9 mmol) was added and the mixture stirred for 1 hour. The white percipitate was filtered and washed with ice cold water (100 ml). The product was dried under vacuum to yield 7.21 g (82.5%). Elemental analysis: % Calcd. for $C_{11}H_{16}N_2O_4$/% Found: C 54.99/54.28; H 6.71/6.48; N 11.66/11.37. M.p. 125°–127° C. $R_f$=0.57 ($CHCl_3/CH_3OH$; 9:1); RP-HPLC: $t_r$=20.4 min and k'=12.3, vydac protein C-18 (0.21×15 cm) 5μ; 214 nm; A: 1.0% TFA in water-acetonitrile (19:1), B: 0.1% TFA in acetonitrile using gradient of 5–20% B in 30 min and a flow rate of 1.5 ml/min. $^1$H-NMR ($CD_3OD$) in δ ppm: 1.34 (s, 9H, $(CH_3)_3C$); 3.22 (q, 2H, $CH_2$—NH); 3.58 (q, 2H, $CH_2$—N); 6.79 (s, 2H, CH=CH).

EXAMPLE 4

N-Maleoyl ethylenediamine trifluoroacetate (VII)

N-tert-butyloxycarbonyl-N'-maleoyl ethylenediamine (VI) (2 g, 8.23 mmol) was dissolved in dichloromethane (40 ml) followed by the addition of TFA (20 ml). The reaction mixture was left 30 min at room temperature protected with $CaCl_2$. The residue obtained after evaporation of the solvent was treated with dry ether and the precipitate formed was collected by filtration. The white solid was dried under vacuum to yield 2.04 g (100%).

EXAMPLE 5

N-Maleoyl-N'-3-(4-hydroxyphenyl)propanoyl ethylenediamide (VIII)

A mixture of N-maleoyl ethylenediamine trifluoroacetate (VII) (0.457 g, 1.8 mmol) and N-succinimidyl-3-(4-hydroxyphenyl)-propionate (0.474 g, 1.8 mmol) dissolved in 2% pyridine solution in DMF (0.5 ml). The pH was adjusted to 8.5 by the addition of diisopropylethylamine (about 0.31 ml, 1.8 mmol) and the mixture was left to stir at room temperature for 24 hours. After removal of solvent under reduced pressure the residue obtained was dissolved in ethylacetate (30 ml) and consequtively extracted with $NaHCO_3$, $KHSO_4$ and brine. The organic phase was dried over $MgSO_4$, filtered and the solvent removed under reduced pressure to yield crude oil (0.3 g). The crude material was purified by HPLC: Delta PrepPack 500 Vydac protein C-18 (15μ) gradient of 0–20% in 150 min and a flow rate of 100 ml/min. A: 0.1% TFA in water-acetonitrile (19:1), B: 0.1% TFA in acetonitrile. Yeild 225 mg (43%). RP-HPLC: $t_r$=14.3 and k'=9.2; Vydac protein C-18 (0.21×15 cm) 5μ; 214 nm; A: 0.1% TFA in water-acetonitrile (19:1), B: 0.1% TFA in acetonitrile using gradient of 0–50% B in 30 min and a flow rate of 1.5 ml/min. FAB-MS: Mw calcd. for $C_{15}H_{16}N_2O_4$ 288, found; 289. Elemental analysis: % Calcd. for $C_{15}H_{16}N_2O_4$ 0.5 $H_2O$ 0.296 Found C 60.16/60.60; H 5.17/5.72; N 9.17/9.42. $^1$H-NMR (DMSOd6) in δ ppm: 2.20 (t, 2H, $CH_2$-CO); 2.62 (t, 2H, $CH_2$-Ar); 3.18 (q, 2H, $CH_2$-NH); 3.43 (t, 2H, $CH^2$-N); 6.64 (d, 2H, Ar); 6.94 (d, 2H, Ar); 7.10 (s, 2H, CH=CH); 7.91 (t, H, NH); 9.12 (s, H, OH).

EXAMPLE 6

N-Maleoyl-N'-3-(4-Hydroxy-3-iodophenyl)propanoyl ethylenediamide (XI)

A mixture of N-maleoyl ethylenediamine trifluoroacetate (VII) (0.305 g, 1.2 mmol) and N-succinimidyl-3-(4-hydroxy-3-iodophenyl)propionate (0.425 g, 1.2 mmol) dissolved in 2% pyridine solution in DMF (0.5 ml). The pH was adjusted to 8.5 by the addition of diisopropylethylamine (about 0.21 ml, 1.2 mmol) and the mixture was left to stir at room temperature for 24 hours. The reaction mixture was diluted with water (30 ml) and lyophilized to yield a crude oil (0.4 g). The crude material was purified by HPLC: Delta PrepPack 500 Vydac protein C-18 (15μ); gradient of 0–20% in 150 min and a flow rate of 100 ml/min.; A: 0.1% TFA in water-acetonitrile (19:1), B: 0.1% TFA in acetonitrile. Yield 207 mg (45%). RP-HPLC: $t_r$=19.2 and k'=12.7; Vydac protein C-18 (0.21×15 cm) 5μ; 214 nm; A: 0.1% TFA in water-acetonitrile (19:1), B: 0.1% TFA in acetonitrile using gradient of 0–50% B in 30 min and a flow rate of 1.5 ml/min. FAB-MS; Mw clacd. for $C_{15}H_{15}N_2O_4I$ 414, found; 415. Elemental analysis: % Calcd. for $C_{15}H_{15}N_2O_4I$.0.5 $H_2O$/% Found: C 42.55/42.38; H 3.78/3.19; N 6.62/650. $^1$H-NMR (DMSOd6) in δ ppm: 2.21 (t, 2H, $CH_2$-CO); 2.62 (t, 2H, $CH_2$-Ar); 3.17 (q, 2H, $CH_2$-NH); 3.42 (t, 2H, $CH^2$-N); 6.77 (d, H, Ar); 6.98 (m, H, Ar); 7.00 (s, 2H, CH=CH); 7.46 (m, H, Ar); 7.91 (t, H, NH); 10.03 (s, H, OH).

EXAMPLE 7

[Cys$^{35}$(S-2'-(N-succinyl-$\beta$-alanyl-3-iodotyramide)]PTHrP (1-35)NH$_2$ (analog 1A)

A mixture of [Cys$^{35}$]PTHrP(1-35)NH$_2$ (analog 1) (20.8 mg, 5 $\mu$mol) and 3'-maleimidopropion-3-iodotyramide (IV) (11.83 mg, 28.6 $\mu$mol) was dissolved in DMF (1 ml). It was allowed to stir at room temperature for 48 hours followed by removal of solvent under reduced pressure. The residue obtained was purified byHPLC: Vydac protein C-18 (15$\mu$, 2.2$\times$25 cm); 214 nm; gradient of 0–50% B in 100 min and a flow rate of 35 ml/min. A: 0.1% TFA in water-acetonitrile (19:1), B: 0.1% TFA in acetonitrile. Yield 15 mg (66%).

EXAMPLE 8

Ac[Cys$^8$(S-2'-(N-succinyl-$\beta$-alanyl-3-idotyramide), Leu$^{11}$, D-Trp$^{12}$]-PTHrP(8-34)NH$_2$ (analog 2A)

A mixture of Ac[Cys$^8$, Leu$^{11}$, D-Trp$^{12}$]PTHrP-(8-34)NH$_2$ (analog 2) (17 mg, 5 $\mu$mol) and 3'-maleimidopropion-3-iodotyramide (IV) (10.36 mg, 25 $\mu$mol) was dissolved in DMF (200 $\mu$l). Following the procedure described above for analog 1A the yield obtained was 14.3 mg (76%).

EXAMPLE 9

Ac[Cys$^8$(S-2'-N-succinyl-N'-3-(4-Hydroxy-3-iodophenyl) propanoyl-ethylenediamide), Leu$^{11}$,D-Trp$^{12}$]PTHrP(8-34)NH$_2$ (analog R2A)

A mixture of Ac[Cys$^8$, Leu$^{11}$, D-Trp$^{12}$]PTHrP-(8-34)NH$_2$ (analog 2) (17 mg, 5 $\mu$mol) and N-Maleoyl-N'-3-(4-Hydroxy-3-iodophenyl)propanoyl ethylenediamide (VIII) (10.36 mg, 25 $\mu$mol) were dissolved in DMF (200 $\mu$l) and left to stir overnight at room temperature. Following the procedure described above for analog 1A the yeild obtained was 10.8 mg (57%).

EXAMPLE 10

[Nle$^{8,18}$,Lys$^{13}$ ($\epsilon$-Biotinyl),Tyr$^{34}$,Cys$^{35}$(S-2'-(N-succinyl-$\beta$-alanyl-3-iodotyramide)]bPTH(1-35)NH$_2$ (analog 3A)

A mixture of [Nle$^{8,18}$,Lys$^{13}$ ($\epsilon$-Biotinyl), Tyr$^{34}$,Cys$^{35}$]bPTH(1-35)NH$_2$ (3) (23.6 mg, 5.3 $\mu$mol) and 3'-maleimidopropion-3-iodotyramide (IV) (4.19 mg, 10.1 $\mu$mol) was dissolved in DMF (400 $\mu$l) and left overnight at room temperature. Following the procedure described above for analog 1A the yeild obtained was 12.3 mg (48%).

EXAMPLE 11

Radioiodination of Thiol Containing Peptides

A: Radioiodination of tyramine: Tyramine (10 $\mu$g, 0.73 nmol) dissolved in 100 mM phosphate buffer pH 7.4 (50 $\mu$l) was added to Iodo-Gen (10 $\mu$g, 0.23 nmol, immobilized in a 12$\times$75 mm borosilicate tube) followed by Na$^{125}$I (2.0 mCi, 20 $\mu$l. purchased from Amersham, specific activity 2200 Ci/mmol). The reaction was carried out for 10 min at room temperature. The reaction mixture was transfered to a second borosilicate tube (12$\times$75 mm) containing acetonitrile (100 $\mu$l) and left for 10 min at room temperature.

B: Preparation of 3'-maleimidopropion-3-[$^{125}$I]-iodotyramide (IV*)

I. Via acylation of 3-[$^{125}$I]-iodotyramine (II*) by N-succinimidyl 3-maleimidopropionate (III): A solution of N-succinimidyl 3-maleimidopropionate (III) (500 $\mu$g, 1.9 $\mu$mol) dissolved in acetonitrile (100 $\mu$l) was added to the reaction mixture, described in A above, and left for 60 min at room temperature. The solution was then diluted with 0.1% TFA (600 $\mu$l) and the mixture removed and injected onto HPLC. Conditions for HPLC are as follows: Vydac protein C-18 (5$\mu$, 0.21$\times$15 cm) column. Solution A-0.1% TFA; solution B-0.1% TFA in acetonitrile. Flow rate was 1 ml/min. Absorbance was monitored at 214 nm and radioactivity was monitored via a flow through gama detector (Beckman model 170 radioiotope detector). The gradient used was 0–10 min, 10% B, 10–40 min, 10–60% B. The major radioiodinate peak, corresponding to the anticipated product (t$_r$=28 min, k'=19) was pooled (0.5 min fractions) into a borosilicate tube (12$\times$75 mm).

II. Via direct radioiodination of 3-maleimidopropion-tyramide (V): A solution of 3-maleimidopropiontyramide (V) (50 $\mu$g, 2 $\mu$mol) in 100 mM sodium phosphate buffer (100 $\mu$l) pH 6.5 was added to Iodo-Gen (10 $\mu$g, 0.23 nmol, immobilized in a 12$\times$75 mm borosilicate tube) followed by Na$^{125}$I (2.0 mCi, 20 $\mu$l) and incubated for 10 min at room temperature. The reaction mixture was then diluted with 0.1% TFA (600 $\mu$l) and purified as described in B-I.

C: Radiolabeling of peptide with IV*: Either [Cys$^{35}$]PTHrP(1-35)NH$_2$ (analog 1), or Ac[Cys$^8$, Leu$^{11}$, D-Trp$^{12}$]PTHrP(8-34)NH$_2$ (analog 2) or [Nle$^{8,18}$,Lys$^{13}$($\epsilon$-Biotinyl), Tyr$^{34}$,Cys$^{35}$]bPTH(1-35) NH$_2$ (analog 3) (at least 50 $\mu$g) was dissolved in twice the volume of water. An aliquot of this solution (20 $\mu$l) was added to the pooled HPLC purified radiolabeling reagent IV* (described in C above) and the tube was capped with a needle pierce cap. The reaction mixture was then concentrated in a Speed Vac (Savant) for 60 min. The concentrated solution was brought to pH 6.5 by addition of small aliquots (10 $\mu$l) of 1M Hepes, pH 7.5, and testing pH with Universal pH paper. After reaching pH 6.5 the remainder of the peptide solution (up to 60 $\mu$g) was added to the reaction tube which was then stirred overnight at 4° C. The reaction mixture was seperated on Vydac protein C-18 column (0.21$\times$15 cm) (buffers A and B as above) using gradient of 30–35% B over 30 min and a flow rate of 1 ml/min (t$_r$=11.9 min, k'=4.1; t$_r$=23.8 min, k'=8.5; t$_r$=20.4 min k'=7.7 for radiolabled analogs 1A*–3A*, respectively). The peak radioactive fractions (0.5 min fractions) were pooled and diluted with an equal volume of 2% BSA in 50 mM Hepes, pH 7.5, subaliquoted into Eppendorf vials and stored at −70° C.

D. Preparation of N-Maleoyl-N'-3-(4-hydroxyphenyl) propanoyl ethylenediamide (IX*) via prelabeled N-succinimidyl 3-(4-hydroxy-3-[$^{125}$I]-iodophenyl) propionate: N-succinimidyl 3-(4-hydroxy-3-[$^{125}$I]-iodophenyl)propionate was dissolved in 100 mM NaPO$_4$, pH 7.4 (80 $\mu$l). The N-maleoyl ethylenediamine trifluoroacetate (VII) (500 ug) dissolved in acetonitrile (100 $\mu$l) was added and incubated at room temperature for 60 min. The reaction was stopped by the addition of 0.1% TFA (500 $\mu$l) and the mixture was separated by HPLC using a Vydac Protein C-18 column (0.21$\times$15 cm) (buffers A and B as above) using gradient of 10–50% B over 30 min and a flow rate of 1 ml/min (t$_r$=25 min, k'=8.8) Fractions (0.5 min) were collected and counted and the hottest fractions pooled and concentrated in a Savant Speed Vac for 2 h. After concentration the solution was brought to a pH of about 6.5 by the addition of 1M Hepes, pH 7.5 (75 μl).

E. Radiolabeling of PTHrP antagonist 2A with IX*: Peptide 2A (100 mg) in water (100 ml) was added to a solution of radioligand IX* (see preceding section D) and the reaction was incubated overnight at 4° C. with stirring. After incubation the mixture was separated by HPLC as described above using gradient of 31-39% B over 30 min (t$_r$=23.3 min, k'=8). Peak radioactive fractions (0.5 min fractions) were pooled and diluted with an equal volume of 2% BSA in 50 mM Hepes, pH 7.5, subaliquoted into Eppendorf vials and stored at −70° C.

Table I disclosed the binding and cyclase activity of agonist- and antagonist-adducts derived from PTH and PTHrP sequences with bovine renal cortical membranes and B10 cells.

-continued

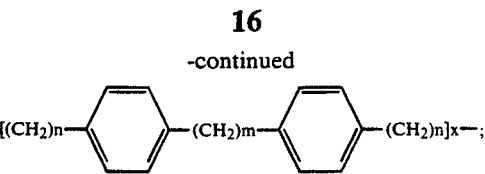

R$^2$ is H or a radionuclide selected from $^{122}$I, $^{123}$I, $^{125}$I, $^{131}$I, $^{75}$Br, $^{77}$Br, $^{82}$Br, or $^{211}$At;

n is 1 or 2;
m is 0 to 2; and
x is 1 or 2.

2. The compound of claim 1, which is:

TABLE I

Binding and Cyclase Activity of Agonist- and Antagonist Adducts Derived from PTH and PTHrP Sequences with Bovine Renal Cortical Membranes and B10 Cells

| nmbl/mg | Analog | Human Osteosarcoma B10 Cell Line | | | Bovine Renal Cortical Membranes | | |
|---|---|---|---|---|---|---|---|
| | | Cyclase$^a$ | | Binding$^b$ | Cyclase$^c$ | | Binding$^d$ |
| | | Km (nM) | Ki (nM) | Kb (nM) | Km (nM) | Ki (nM) | Kb (nM) |
| | [Cys$^{35}$ (S-Add)]PTHrP (1-35)NH2 (1A) | 0.5 ± 0.04 | — | 4.2 ± 0.7 | 36 ± 7 | | 14 ± 2     5 |
| 124.5 | [Nle$^{8,18}$,Lys$^{13}$(-Biotinyl),Try$^{34}$,-Cys$^{35}$(S-Add)]bPTH (1-35)NH2 (3A) | 0.5 ± 0.06 | | 1.7 ± 0.2 | 6.4 ± 0.7 | | 2 ± 0.2     2 |
| 168.5 | Ac[Cys$^8$(S-Add),Leu$^{11}$, D-Trp$^{12}$]-PTHrP(8-34) NH2 (2A) Ac[Cys$^8$(S-retroAdd), Leu$^{11}$,D-Trp$^{12}$-PTHrP (8-34)2 (R2A) | | 2.8 ± 1 | 2.4 ± 0.5 | | 22 ± 5 | ·2 ± 0.1     1 |

Values are the mean ± SEM from at least three separate experiments.
$^a$Inhibiting binding of 95 pM [Nle$^{8,18}$, momo-[$^{125}$I Tyr$^{34}$(3-I)]bPTH(1-34)NH2.
$^b$Antagonizing 0.25 nM [Nle e$^{8,18}$, Tyr$^{34}$]bPTH(1-34)NH2
$^c$Inhibiting binding of 25 nM [Nle$^{8,18}$, mono-[$^{125}$I]-Tyr$^{34}$(3-I)]bPTH(1-34)NH2.
$^d$Antagonizing 3 nM [Nle$^{8,18}$, Tyr$^{34}$]bPTH(1-34)NH2

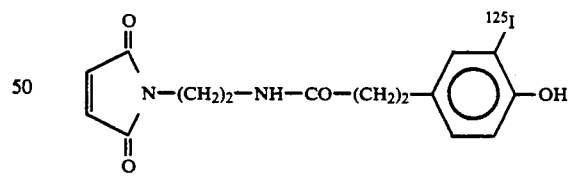

What is claimed is:

1. A compound of Formula I:

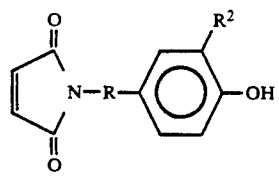

wherein:
R is (CH$_2$)n—NH—CO—(CH$_2$)m, (CH$_2$)n—CO—NH—(CH$_2$)m,

—[(CH$_2$)n—O—(CH$_2$)m—(CH$_2$)n]x,

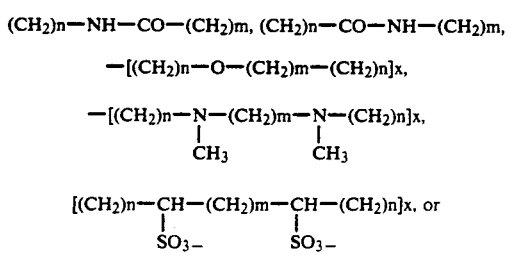

[(CH$_2$)n—CH—(CH$_2$)m—CH—(CH$_2$)n]x, or
         |                |
         SO$_3$−          SO$_3$−

3. The compound of claim 1, which is:

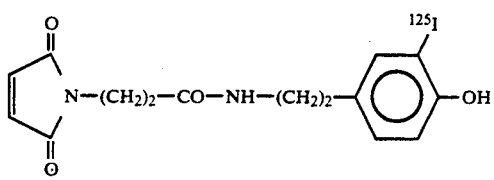

4. A method of detection and quantification of protein receptors in mammalian tissue which comprises administering to a mammal in which such quantification is desired an effective amount of a protein which has been labeled with a compound of claim 1, provided that R$^2$ is other than hydrogen, and thereafter measuring the labeled protein in the mammal with radioimaging techniques.

5. The method of claim 4 wherein the mammal is a human.

6. The method of claim 4 wherein the protein is PTH or PTHrP.

7. A method of diagnostic imaging of tissues bearing protein receptors in a mammal, which comprises administering to the mammal in need of such diagnostic imaging a protein which has been labeled with a compound of claim 1, provided that $R^2$ is other than hydrogen, and thereafter recording a diagnostic image using diagnostic imaging techniques.

8. The method of claim 7, wherein the mammal is a human.

9. The method of claim 7, wherein the protein is PTH or PTHrP.

10. A method of detection and quantification of protein receptors in mammalian tissue which comprises administering to a mammal in which such quantification is desired an effective amount of protein which has been labeled with a compound of claim 2 and thereafter measuring the labeled protein in the mammal with radioimaging techniques.

11. The method of claim 10, wherein the mammal is a human.

12. The method of claim 10, wherein the protein is PTH or PTHrP.

13. A method of diagnostic imaging of tissue bearing protein receptors in a mammal which comprises administering to the mammal in need of such diagnostic imaging a protein which has been labeled with a compound of claim 3 and thereafter recording a diagnostic image using diagnostic imaging techniques.

14. The method of claim 13, wherein the mammal is a human.

15. The method of claim 13, wherein the protein is PTH or PTHrP.

* * * * *